United States Patent [19]
Grollier et al.

[11] Patent Number: 4,823,985
[45] Date of Patent: Apr. 25, 1989

[54] FORMING IN SITU A COMPOSITION CONSISTING OF TWO SEPARATELY PACKAGED CONSTITUENTS AND DISPENSING ASSEMBLY FOR CARRYING OUT THIS PROCESS

[75] Inventors: Jean-Francois Grollier, Paris; Lyonel Peritz, Boulogne; Hervé F. Bouix, Marly le Roi, all of France

[73] Assignee: L'Oreal, Paris, France

[21] Appl. No.: 218,139

[22] Filed: Jul. 13, 1988

Related U.S. Application Data

[63] Continuation of Ser. No. 903,618, Sep. 5, 1986, abandoned.

[30] Foreign Application Priority Data

Sep. 10, 1985 [FR] France ............................ 85 13387

[51] Int. Cl.$^4$ .......................... B67B 7/00; B65D 35/22
[52] U.S. Cl. .......................................... 222/1; 222/94; 222/105; 206/219
[58] Field of Search ................................ 222/94–95, 222/105, 107, 206, 215, 130–131, 134–136, 1; 206/219, 525–526; 424/70–72

[56] References Cited

U.S. PATENT DOCUMENTS

| | | | |
|---|---|---|---|
| Re. 30,516 | 2/1981 | Abegg et al. | 132/7 |
| 2,125,318 | 8/1938 | Salfisberg | 222/94 |
| 3,100,063 | 8/1963 | Henriksen | 222/94 |
| 3,651,931 | 3/1972 | Hsiung | 222/136 X |
| 4,276,263 | 6/1981 | Andersen et al. | 222/107 X |
| 4,280,391 | 7/1981 | Fischer et al. | 206/219 X |
| 4,312,473 | 1/1982 | Hoeller | 229/56 |
| 4,331,264 | 5/1982 | Staar | 222/94 |

FOREIGN PATENT DOCUMENTS

| | | |
|---|---|---|
| 1214424 | 4/1960 | France . |
| 1038492 | 8/1964 | United Kingdom . |
| 1205210 | 9/1970 | United Kingdom . |
| 1491053 | 11/1977 | United Kingdom . |
| 1547025 | 6/1979 | United Kingdom . |

Primary Examiner—Michael S. Huppert
Attorney, Agent, or Firm—Cushman, Darby & Cushman

[57] ABSTRACT

A dispensing assembly for at least two constituents is provided having flexible walls and at least two compartments, including outlet orifices located adjacent to one another so that when the outlet orifices are opened as by cutting, and pressure is applied to the flexible walls, dispensing and immediate mixing of the constituents will be effected; the viscosity and volumes of the constituents are selected to have certain values to enable the dispensing to properly mix the constituents to form a homogenous product.

17 Claims, 1 Drawing Sheet

FORMING IN SITU A COMPOSITION CONSISTING OF TWO SEPARATELY PACKAGED CONSTITUENTS AND DISPENSING ASSEMBLY FOR CARRYING OUT THIS PROCESS

This is a continuation of application Ser. No. 06/903,618, filed Sept. 5, 1986, abandoned.

FIELD OF THE INVENTION

The present invention relates to a process which enables a composition consisting of two separately packaged and simultaneously dispensed constituents A and B to be formed in situ. The present invention also relates to a dispensing assembly for carrying out this process.

The preparation of compositions at the time of use is current practice in a number of fields and, as a general rule, this method of preparation is used whenever the resulting composition has to contain constituents such that, when brought into contact with each other, either they react with each other to give the active product or products which will have to be used immediately, or they bring about a physicochemical imbalance which may result in a fall in the activity of the constituent(s), or they cannot be stored. By constituent, there is understood here either a particular compound, or alternatively a formulation which contains at least one compound capable of being combined with at least one compound of another formulation, the latter formulation being intended to be brought into contact with the former.

PRIOR ART

In the cosmetics field, and in particular in hair-care cosmetics, the mixing of the constituents of compositions such as so-called oxidation dyeing compositions, bleaching compositions, colour-lightening shampoos, and exothermic compositions involving oxidation/reduction systems is carried out only at the time of use, these constituents frequently being grouped together in two sub-combinations.

Also in the cosmetics field, a number of examples are also found illustrating the case of compositions, which could not be combined previously without bringing about a physicochemical imbalance leading to the above-mentioned disadvantages. Mention may be made of various cosmetic treatment compositions based on cosmetic agents having opposite ionic strength.

The preparation of a composition at the time of use is customarily performed by mixing its constituents in a container, after which the resulting mixture is used, for example is applied on a support such as the hair or skin.

In some cases, this intermediate mixing stage can represent on the one hand a cost in equipment, since suitable containers must be provided for carrying out the mixing, and on the other hand wasted time for the user.

Furthermore, this time wastage can sometimes involve either a loss of active component or components, for example by evaporation, which can have an effect on the result expected of the final composition, or a decrease in, or even loss of, the activity of the said composition, in particular if the reaction between the two constituents of the composite is a rapid reaction, as is the case with compounds which react with each other by a catalytic process.

On the other hand, in the case of a slow reaction and/or, moreover, where the constituents have an inherent activity which may be advantageous, the loss of time due to performing the operation of mixing the constituents in question can have the effect of not enabling the benefit to be derived from this inherent activity of the constituents, which activity might develop before the final product was formed.

The case of so-called oxidation hair-dyeing compositions illustrates these disadvantages of the known art for preparing compositions at the time of use.

Such compositions are produced at the time of use by mixing a formulation A, containing at least one oxidation dye, and a formulation B containing hydrogen peroxide. In the hairdressing salon, the operator weighs the amounts of the two formulations A and B which are to constitute the active mixture, and he carries out the said mixing in a bowl using a paint brush or other brush. As regards private individuals, they can obtain commercially the two formulations A and B separately packaged and, for application on the hair, they have to transfer one of these formulations to a container containing the other in order to carry out the mixing. This manipulation can lead to partial evaporation of the ammonia present in the dye formulation A, and this loss of ammonia can adversely affect the qualities of uniformity of the final oxidation dyeing.

Similarly, in hair bleaching, the procedure is also carried out by mixing in a bowl, prior to application on the hair, a formulation A containing ammonia and a formulation B containing hydrogen peroxide. As a result, a partial loss of ammonia can take place, with the likelihood of producing less powerful lightening of colour than that envisaged.

OBJECT OF THE INVENTION

It is an object of the present invention to overcome the above-mentioned disadvantages of the prior art.

SUMMARY OF THE INVENTION

The Applicants have now discovered that, by selecting formulations or constituents A and B of a composition intended to be prepared at the time of use, which parts show specific rheological properties, and by choosing appropriate packaging to contain the constituents A and B separately, but to enable simultaneous and common dispensing of these constituents A and B to be performed, the desired composition could be produced directly on the site of application. Under these conditions the intermediate stage of mixing in a container is eliminated, thereby resulting in a facility of application, a gain in time, an economization on equipment, and a more satisfactory use of some active components.

Furthermore since the constituents A and B of the composition are delivered directly from the packaging to the support, in contrast to the prior art, it becomes possible in the first place in the case of products formed by a rapid reaction, to profit from the optimal activity of these products for which the activity appears to have a tendency to decrease during the period following their chemical formation and in the second place, in the case of products formed by a slow reaction, to profit from the possible inherent activity of the individual constituent or constituents before modification by their interaction. In this latter case, if it was desired to turn the activity inherent in each of these compounds to good account, the application of the composition had to be performed in two stages.

A first aspect of the present invention therefore provides a process for forming a composition in situ by mixing two simultaneously dispensed constituents A and B, this process employing two containers in which the constituents A and B are selected to have, individually and when mixed, respective viscosities $\eta A$, $\eta B$, $\eta A+B$, which, when measured under laminar flow conditions at a rate of 45 s$^{-1}$ using a HAAKE "ROTOVISCO RV 100" viscometer at 25° C., fulfil the following conditions:

| $\eta A$ | $\leq$ | 1,500 cP, |
|---|---|---|
| $\eta B$ | $\leq$ | 1,500 cP, |
| $\eta A - \eta B$ | $\leq$ | 1,000 cP, |
| $\eta A + B$ | $\leq$ | 3,000 cP, | the volumes of the constituents A and B confirming the relationship:

$$0.2 \leq \frac{\text{volume of } A}{\text{volume of } B} \leq 2,$$

the constituents being stored in containers which posses a deformable wall, enabling simultaneous compression to be effected by successive squeezing actions by the user so as to provide for the dispensing of their contents, and which have outflow orifices close together or capable of being brought into proximity with each other and arranged in such a way that the outflow jets meet each other, the said outflow orifices being capable of being opened simultaneously and each having a cross-section of from 0.1 to 75 mm$^2$.

Preferably, the constituents A and B are such that the viscosities $\eta A$, $\eta B$, and $\eta A+B$, measured as stated above, fulfil the following conditions:

| $\eta A$ | $\leq$ | 500 cP, |
|---|---|---|
| $\eta B$ | $\leq$ | 100 cP, |
| $\eta A - \eta B$ | $\leq$ | 300 cP, |
| $\eta A + B$ | $\leq$ | 1,500 cP. |

Advantageously, the orifices are created by a cut of from 3 to 10 mm in length on a glove-finger like zone of the containers.

Preferably also, the constituents A and B have viscosities $\eta A$, $\eta B$, measured under laminar flow conditions at a rate of 450s$^{-1}$ using a HAAKE "ROTOVISCO RV 100" viscometer at 25° C., of less than or equal to 1,000 cP and, more especially, less than or equal to 300 cP.

In an especially advantageous embodiment of the process according to the present invention, two bags of flexible material are selected as containers, the outflow orifice of each bag being by sectioning two end portions of wall facing each other.

Preferably, the outflow orifice of each of the two flexible bags is formed by simultaneous sectioning of an outflow tip common to both bags.

A second aspect of the present invention provides a dispensing assembly for carrying out the process as defined above, this dispensing assembly incorporating two containers respective ones of which contain the two components A and B intended to form one and the same composition by simultaneous dispensing, wherein the containers have, on the other hand, a deformable wall enabling them to be compressed simultaneously by successive squeezing actions by the user in order to provide for the dispensing of their contents, and on the other hand outflow orifices which are close together or capable of being brought into proximity with each other, and arranged in such a way that their outflow jets meet each other, the said outflow orifices being capable of being opened simultaneously and each having a cross-section of from 0.1 to 75 mm$^2$, and in that the constituents A and B possess, individually and when mixed, respective viscosities $\eta A$, $\eta B$ and $\eta A+B$, when measured under low laminar flow conditions at a rate of 45 s$^{-1}$ using a HAAKE "ROTOVISCO RV 100" viscometer at 25° C., which fulfil the following conditions:

| $\eta A$ | $\leq$ | 1,500 cP, |
|---|---|---|
| $\eta B$ | $\leq$ | 1,500 cP, |
| $\eta A - \eta B$ | $\leq$ | 1,000 cP, |
| $\eta A + B$ | $\leq$ | 3,000 cP, | the volumes of the constituents A and B satisfying the relationship:

$$0.2 \leq \frac{\text{volume of } A}{\text{volume of } B} \leq 2,$$

The preferred conditions for the viscosities of constituents A and B are those stated above.

Moreover, in a particular embodiment, each container is a sealed bag of flexible material, the outflow orifice of each bag being able to be formed by sectioning of two bag end wall portions facing each other. In particular, the two independent bags can be united by juxtaposition, that is to say coupled to each other and arranged in a flexible case, and can have a common outflow tip capable of being sectioned to form simultaneously the outflow orifices of said bags.

In an especially preferred embodiment of the dispensing assembly according to a second aspect of the invention, this assembly incorporates a sachet consisting of three superposed sheets joined along their edges, each of the two outer sheets constituting, with the inner sheet, one of the bags of flexible material.

In the case where the assembly is intended for the direct application on the skin and hair of an amount of a cosmetic composition, one of the constituents A or B of said composition advantageously contains at least one foaming agent in a proportion of from 0.1 to 30% by weight, and in particular from 1 to 20% by weight, relative to the total weight of the composition.

According to a preferred embodiment, the dispensing assembly is used for containing and applying a composition consisting of two constituents for colour lightening or coloring hair. In this case, the viscosities $\eta A$, $\eta B$, $\eta A+B$ fulfil the following conditions:

$\eta A$ is comprised between 10 and 800 cps;
$\eta B$ is comprised between 10 and 800 cps;
$\eta A+B$ is comprised between 10 and 800 cps as disclosed hereinafter in example 3.

In particular, these viscosities meet the following requirements:

$\eta A$ is comprised between 10 and 30 cps;
$\eta B$ is comprised between 10 and 30 cps.
$\eta A+B$ is comprised between 10 and 30 cps as disclosed hereinafter in example 4.

BRIEF DESCRIPTION OF THE DRAWINGS

Apart from the arrangements set above, the invention will be better discussed with reference to the attached drawings, but which is in no way restrictive. In the drawings.

DESCRIPTION OF THE PREFERRED EMBODIMENTS

Several embodiments of the invention will now be described so that it will be better understood.

Figure 1:
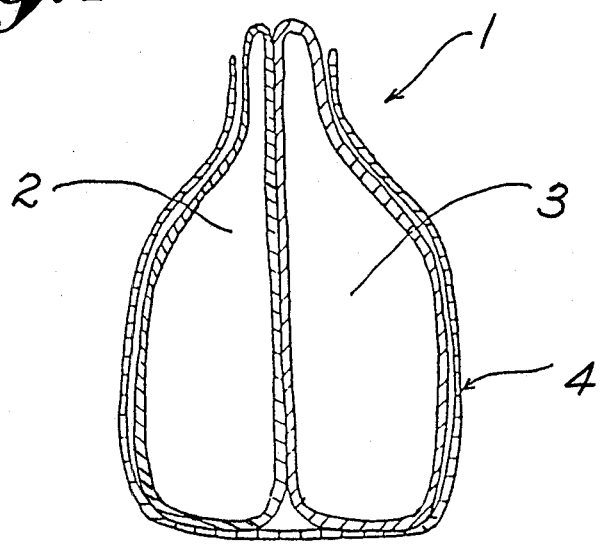
FIG. 1 is a longitudinal, cross-sectional view of a first embodiment of a dispensing assembly incorporating two containers united by juxtaposition and arranged in a flexible case.

In a first embodiment as shown in FIG. 1, the dispensing assembly 1 incorporates two independent bags 2 and 3, respective ones of which contain the two components A and B. The wall of each bag is deformable and the outflow orifices are capable of being opened simultaneously. These two bags, 2 and 3, are united by juxtaposition in a flexible case 4.

Figure 2:
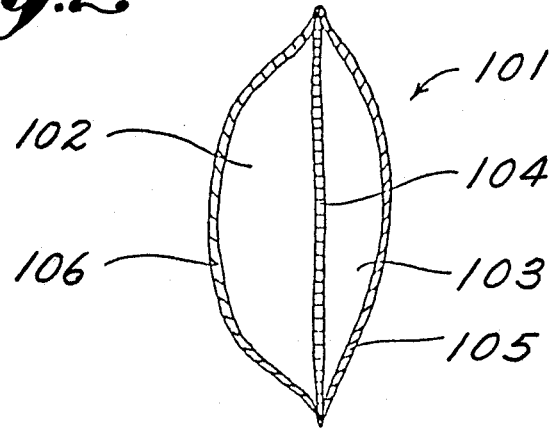
FIG. 2 is a longitudinal, cross-sectional view of a second embodiment of a dispensing assembly according to the present invention, incorporating a double-sachet comprising two bags.

According to a second embodiment as shown in FIG. 2, the dispensing assembly 101 incorporates a double-sachet consisting of three superposed sheets 104, 105 and 106 joined along their edges, each of the two outer sheets 105, 106 constituting, with the inner sheet 104, one of the bags 102 or 103 of flexible material.

EXAMPLE 1

To be able to apply a self-heating disentangling lotion, formed by mixing two separately packaged and simultaneously dispensed constituents A and B, directly on a head of hair, the procedure adopted is as follows:

The first step is the separate preparation of each of the two constituents A and B, which are formulated as follows:

| CONSTITUENT A | |
|---|---|
| Sodium metabisulphite | 4 g |
| Cationic polymer consisting of repeated units represented by the following formula: | 0.8 g |

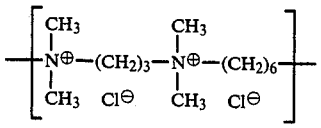

| | |
|---|---|
| and prepared according to French Patent Specification No. 2,270,846 | |
| Methyl para-hydroxybenzoate | 0.1 g |
| Water qs | 100 g |
| CONSTITUENT B | |
| "200 volumes" hydrogen peroxide | 6 g |
| Acetanilide | 0.1 g |
| Phosphoric acid qs | pH 3 |
| Water qs | 100 g |

The viscosities under laminar flow conditions at a low rate of 45 s$^{-1}$, $\eta A$, $\eta B$ and $\eta A+B$, of the constituent A, the constituent B and the mixture thereof, respectively, are measured using a HAAKE "ROTOVISCO RV 100" viscometer at 25° C., and the resulting volume obtained for each of these three viscosities is 8 cP.

10 g of constituent A and 10 g of constituent B are packaged in each of the compartments of a sachet having a tip which is common to both compartments and which has the form of a glove finger 3 mm wide; said sachet consists of three superposed sheets joined along their edges except at the end of the common tip, so as to permit filling. After filling, the sachet is closed by a weld formed at the above-mentioned end.

For application of the lotion, the said tip is sectioned by a transverse cut, which enables two adjacent outflow orifices to be formed. The sachet sectioned in this manner is placed above the head of hair to be treated and inverted at the same time as the wall is compressed manually to enable its contents to flow out; this outflow hence takes place in the form of two essentially intermingled jets. The bringing of the two constituents A and B into contact, and their application, are hence simultaneous.

After this application, which is carried out on clean hair following shampooing, the mixture is kneaded for a few seconds on the hair to make it homogeneous. Since the reaction which takes place between the active constituents of A and B is exothermic, a sensation of heat is felt by the subject as soon as the mixture is applied. Disentangling of the wet hair is easy. Setting is then carried out. After being dried, the hair is easy to disentangle; it is silky and shiny.

EXAMPLE 2

To be able to apply a hair-bleaching composition, formed by mixing two separately packaged and simultaneously dispensed constituents A and B, directly on a head of hair, the procedure adopted is as follows:

The first step is the separate preparation of each of the two constituents A and B, which are formulated as follows:

| CONSTITUENT A | |
|---|---|
| Oxyethylenated nonylphenol (4 moles of ethylene oxide) | 20 g |
| Oxyethylenated nonylphenol (9 moles of ethylene oxide) | 18 g |
| Coconut diethanolamide | 10 g |
| Ethyl alcohol | 5 g |
| Propylene glycol | 11 g |
| Ethylenediaminetetraacetic acid | 0.2 g |
| Ammonia solution containing 20% of NH$_3$ | 10 g |
| Water qs | 100 g |
| CONSTITUENT B | |
| Constituent B consists of an oxydizing milk containing "20 volumes" H$_2$O$_2$, of composition: | |
| Cetyl alcohol | 1 g |
| Oxyethylenated cetyl alcohol (10 moles of ethylene oxide) | 1.5 g |
| Phenacetin | 0.1 g |
| Ethylenediaminetetraacetic acid | 0.02 g |
| Phosphoric acid qs pH 3 | |
| "200 volumes" hydrogen peroxide | 12 g |
| Water qs | 100 g |

The viscosities $\eta A$, $\eta B$ and $\eta A+B$, as defined in Example 1, are then measured.

The following results are obtained:

| | |
|---|---|
| $\eta A$ | 80 cP, |
| $\eta B$ | 200 cP, |
| $\eta A + B$ | 450 cP. |

35 g of constituent A and 35 g of constituent B are packaged in two independent sachets arranged in a flexible case. The procedure is then as described in Example 1, except that the line of cut of the sachet tip is 7 mm long.

After the application, on unwashed hair, of the mixture of these two constituents A and B directly from the above-mentioned two sachets, the mixture, in which the two constituents A and B are combined to form a gelified hair-care composition having the desired properties, is kneaded for a few minutes on the head of hair to make it homogeneous. The hair is left exposed to the mixture for 30 minutes and then rinsed; a lightening of approximately two tones is obtained relative to the initial colour of the hair, which corresponds to a bleaching of moderate intensity.

EXAMPLE 3

To be able to apply an oxidation hair-dyeing composition, formed by mixing two separately packaged and simultaneously dispensed constituents A and B, directly on a head of hair, the procedure adopted is as follows:

The first step is the separate preparation of each of the two constituents A and B, which are formulated as follows:

| CONSTITUENT A | | |
|---|---|---|
| Ammonium lauryl sulphate | 15 | g of active substances |
| Coconut diethanolamide | 5 | g |
| Hydroxyethylcellulose sold under the name "NATROSOL 250 HHR" by "HERCULES" | 0.5 | g |
| Ammonia solution containing 20% of $NH_3$ | 10 | g |
| Ethylenediaminetetraacetic acid | 0.2 | g |
| 2-Methyl-1,4-diaminobenzene dihydrochloride | 0.64 | g |
| 1-Amino-4-hydroxybenzene | 0.10 | g |
| 1,3-Dihydroxybenzene | 0.20 | g |
| 1-Hydroxy-3-aminobenzene | 0.60 | g |
| 6-Aminobenzomorpholine dihydrochloride | 0.045 | g |
| Hydroquinone | 0.174 | g |
| Sodium bisulphite, 35° Be | 1.3 | g |
| Water qs | 100 | g |
| CONSTITUENT B | | |
| Constituent B consists of an oxidizing milk containing "20 volumes" $H_2O_2$, of composition: | | |
| Cetyl alcohol | 1 | g |
| Oxyethylenated cetyl alcohol (10 moles of ethylene oxide) | 1.5 | g |
| Phenacetin | 0.1 | g |
| Ethylenediaminetetraacetic acid | 0.02 | g |
| Phosphoric acid qs pH 3 | | |
| "200 volumes" hydrogen peroxide | 12 | g |
| Water qs | 100 | g |

The viscosities $\eta A$, $\eta B$ and $\eta A + B$, as defined in Example 1, are then measured, proceeding as described in that example, and the following results are obtained:

| $\eta A$ | = | 670 cP |
|---|---|---|
| $\eta B$ | = | 200 cP |
| $\eta A + B$ | = | 125 cP. |

The procedure is then as described in Example 2, except that one sachet contains 40 g of constituent A and the other 40 g of constituent B, and that the tip of the two sachets is sectioned according to a cut 10 mm long. Kneading on the head of hair provides for the formation of a homogeneous foaming gel. After the hair has been exposed to this gel for 30 minutes and then rinsed, it is observed that the hair, which was originally dark chestnut brown, has taken on an ashen light chestnut shade.

EXAMPLE 4

To be able to apply a slightly colour-lightening shampoo, formed by mixing two separately packaged and simultaneously dispensed constituents A and B, directly on a head of hair, the procedure adopted is as follows:

The first step is the separate preparation of each of the two constituents A and B, which are formulated as follows:

| CONSTITUENT A | | |
|---|---|---|
| Oxyethylenated sodium lauryl ether sulphate (2 moles of ethylene oxide) | 7.5 | g of active substances |
| Coconut diethanolamide | 3 | g |
| Hydroxyethyl cellulose sold under the name "NATROSOL 250 HHR" by "HERCULES" | 0.1 | g |
| Propyl para-hydroxybenzoate | 0.05 | g |
| Methyl para-hydroxybenzoate | 0.10 | g |
| Sodium hydroxide qs pH 10 | | |
| Water qs | 100 | g |
| CONSTITUENT B | | |
| An oxidizing milk is prepared containing "20 volumes" $H_2O_2$, as follows: | | |
| Cetyl alcohol | 1 | g |
| Oxyethylenated cetyl alcohol (10 moles of ethylene oxide) | 1.5 | g |
| Phenacetin | 0.1 | g |
| Ethylenediaminetetraacetic acid | 0.02 | g |
| Phosphoric acid qs Ph 3 | | |
| "200 volumes" hydrogen peroxide | 12 | g |
| Water qs | 100 | g |

These viscosities $\eta A$, $\eta B$ and $\eta A + B$, as defined in Example 1, are then measured as described in that example, and the following results are obtained:

| $\eta A$ | 20 cP |
|---|---|
| $\eta B$ | 13 cP |
| $\eta A + B$ | 13 cP. |

10 g of constituent A and 10 g of constituent B are packaged in each of the compartments of a sachet of the same type as that defined in Example 1, and the procedure is as described in that example for the application of shampoo on the air, except that the tip of the sachet is sectioned according to a cut 8 mm long. After application of the composition, the mixture is kneaded for a few seconds to ensure the formation of a homogeneous mixture. The hair is left exposed for 5 minutes and rinsed. It is observed that, after five or six applications of the shampoo, a slight lightening in colour of the hair is obtained.

We claim

1. A process for forming a composition in situ by mixing two constituents A and B to be simultaneously dispensed and used for hair coloration comprising the steps of:
    (a) taking two containers having a wall which is sufficiently deformable to enable simultaneous compression to be effected by successive squeezing actions by the user so as to dispense the contents of said containers and having outflow orifices adapted to be positioned adjacent to one another so that the constituents will contact each other upon dispensing with their outflow jets meeting each other, said outflow orifices being adapted to be opened simultaneously and each having a cross-section of from 0.1 to 75 $mm^2$;

(b) selecting constituents A and B which have individually and when mixed respective viscosities A, B, A+B, which, when measured under laminar flow conditions at a rate of 45 s$^{-1}$ using a HAAKE "ROTOVISCO RV 100" viscometer at 25° C., fulfil the following conditions:

| | | |
|---|---|---|
| $\eta A$ | $\leq$ | 1,500 cP, |
| $\eta B$ | $\leq$ | 1,500 cP, |
| $\eta A - \eta B$ | $\leq$ | 1,000 cP, |
| $\eta A + B$ | $\leq$ | 3,000 cP, | one of said constituents including a foaming agent in a quantity between 0.1 and 30% by weight of the total weight of the composition;

(c) taking volumes of the constituents A and B which satisfy the relationship:

$$0.2 \leq \frac{\text{volume of } A}{\text{volume of } B} \leq 2;$$

and (d) packaging the constituents A and B separately in respective ones of said containers.

2. A process according to claim 1, wherein the constituents A and B have viscosities $\eta A$, $\eta B$ and $\eta A+B$ which, when measured as stated in claim 1, fulfil the following conditions:

| | | |
|---|---|---|
| $\eta A$ | $\leq$ | 500 cP |
| $\eta B$ | $\leq$ | 500 cP |
| $\eta A - \eta B$ | $\leq$ | 300 cP |
| $\eta A + B$ | $\leq$ | 1,500 cP. |

3. A process according to claim 1, wherein the constituents A and B individually have viscosities $\eta A$, $\eta B$, measured under laminar flow conditions at a rate of 450 s$^{-1}$ using a HAAKE "ROTOVISCO RV 100" viscometer at 25° C., of no greater than 1,000 cP.

4. A process according to claim 3, wherein said viscosities $\eta A$, $\eta B$, measured as stated in claim 3, are no greater than 300 cP.

5. A process according to claim 1, comprising selecting as said containers two bags of a flexible material with the outflow orifice of each bag formed by sectioning two end wall portions facing each other.

6. A process according to claim 5, wherein the bags are such that the outflow orifice of each of the two flexible bags is able to be formed by simultaneous sectioning of an outflow tip common to both bags.

7. A dispensing assembly for carrying out the process of claim 1, comprising:
(a) first and second containers having:
(aa) a deformable wall enabling them to be compressed simultaneously by successive squeezing actions by the user in order to provide for the dispensing of their contents, and
(ab) means defining outflow orifices adapted to become close together in such a way that the outflow jets meet each other, the said outflow orifices being capable of being opened simultaneously and each having a cross-section of from 0.1 to 75 mm$^2$; and
(b) first and second constituents A and B which are intended to form one and the same composition by simultaneous dispensing, said first and second constituents being packaged in said first and second containers, respectively, wherein said first and second constituents A and B have, individually and when mixed, respective viscosities $\eta A$, $\eta B$ and $\eta A+B$, when measured under laminar flow conditions at a flow rate of 45 s$^{-1}$ using a HAAKE "ROTOVISCO RV 100" viscometer at 25° C., which fulfil the following conditions
one of said constituents including a foaming agent in a quantity between 0.1 and 30% by weight of the total weight of the composition:

| | | |
|---|---|---|
| $\eta A$ | $\leq$ | 1,500 cP |
| $\eta B$ | $\leq$ | 1,500 cP |
| $\eta A - \eta B$ | $\leq$ | 1,000 cP |
| $\eta A + B$ | $\leq$ | 3,000 cP | said first and second constituents being packaged in volumes satisfying the relationship:

$$0.2 \leq \frac{\text{volume of } A}{\text{volume of } B} \leq 2;$$

and

8. A dispensing assembly according to claim 7, wherein said first and second constituents A and B have viscosities $\eta A$, $\eta B$ and $\eta A+B$ which fulfil the following conditions:

| | | |
|---|---|---|
| $\eta A$ | $\leq$ | 500 cP |
| $\eta B$ | $\leq$ | 500 cP |
| $\eta A - \eta B$ | $\leq$ | 300 cP |
| $\eta A + B$ | $\leq$ | 1,500 cP. |

9. A dispensing assembly according to claim 7, wherein the first and second constituents A and B individually have viscosities $\eta A$, $\eta B$, measured under laminar flow conditions at a rate of 450 s$^{-1}$ using a HAAKE "ROTOVISCO RV 100" viscometer at 25° C., of no greater than 1,000 cP.

10. A dispensing assembly according to claim 9, wherein said viscosities are no greater than 300 cP.

11. A dispensing assembly according to claim 10, wherein each container is a sealed bag of flexible material, the outflow orifice of said bag being adapted to be formed by sectioning of two end wall portions of said bag, facing each other.

12. A dispensing assembly according to claim 11, wherein the two bags have a common outflow tip adapted to be sectioned to form simultaneously the outflow orifices of the sealed bags.

13. A dispensing assembly according to claim 11, wherein the bags comprise a sachet consisting of three superposed sheets joined along their edges, each of the two outer sheets constituting, with the inner sheet, one of said bags of flexible material.

14. A dispensing assembly according to claim 12, wherein the bags comprise a sachet consisting of three superposed sheets joined along their edges, each of the two outer sheets constituting, with the inner sheet, one of said bags of flexible material.

15. A dispensing assembly according to claim 11, comprising two independent sachets united by juxtaposition, and a flexible case enclosing said sachets.

16. A dispensing assembly according to claim 7, wherein said proportion of the foaming agent is from 1 to 20%.

17. The process as claimed in claim 1 wherein the proportion of foaming agent by weight with respect to the total weight of the composition is between 1 and 20%.

* * * * *